(12) United States Patent
Tu et al.

(10) Patent No.: US 11,583,270 B2
(45) Date of Patent: Feb. 21, 2023

(54) NEEDLE SET OF LAPAROSCOPIC SURGERY AND KNOTTING DEVICE THEREOF

(71) Applicant: MatrixLabs Medical Co., Ltd., New Taipei (TW)

(72) Inventors: Fungchao Tu, New Taipei (TW); WenYih Wu, Taipei (TW); Kuei-Hua Chen, Kaohsiung (TW)

(73) Assignee: MATRIXLABS MEDICAL CO., LTD, New Taipei (TW)

( * ) Notice: Subject to any disclaimer, the term of this patent is extended or adjusted under 35 U.S.C. 154(b) by 342 days.

(21) Appl. No.: 17/070,077

(22) Filed: Oct. 14, 2020

(65) Prior Publication Data

US 2022/0110625 A1    Apr. 14, 2022

(51) Int. Cl.
*A61B 17/04* (2006.01)
*A61B 17/062* (2006.01)
*A61B 17/00* (2006.01)

(52) U.S. Cl.
CPC ........ *A61B 17/0469* (2013.01); *A61B 17/062* (2013.01); *A61B 2017/00367* (2013.01); *A61B 2017/0474* (2013.01)

(58) Field of Classification Search
CPC .............. A61B 17/0469; A61B 17/062; A61B 17/00367; A61B 17/0474; A61B 17/00473
See application file for complete search history.

(56) References Cited

U.S. PATENT DOCUMENTS

| | | | |
|---|---|---|---|
| 9,867,608 B1* | 1/2018 | Shelton, IV | A61B 17/0469 |
| 2006/0069396 A1* | 3/2006 | Meade | A61B 17/0482 606/144 |
| 2016/0367238 A1* | 12/2016 | Deck | A61B 17/0469 |
| 2018/0206832 A1* | 7/2018 | Greeley | A61B 1/32 |
| 2021/0212688 A1* | 7/2021 | Tapia Espriu | A61B 17/10 |

FOREIGN PATENT DOCUMENTS

| | | |
|---|---|---|
| CN | 208573778 U | 3/2019 |
| WO | WO2020117687 A1 | 6/2020 |

* cited by examiner

*Primary Examiner* — Phong Son H Dang
(74) *Attorney, Agent, or Firm* — Alan D. Kamrath; Karin L. Williams; Mayer & Williams PC (57) ABSTRACT

The present invention reveals a needle set of laparoscopic surgery and knotting device thereof, the needle set comprising a body and an axis sleeve. Near the body side is formed a barrier, and the other side have a concave groove. The axis sleeve is hollow tube and fixedly run through the body. Therefore the needle set can axial insert into to the axis sleeve, and achieve the effect that minimizing the complicate of overall structure, reducing the length of a knotting device, and more convenient to operate.

9 Claims, 7 Drawing Sheets

NEEDLE SET OF LAPAROSCOPIC SURGERY AND KNOTTING DEVICE THEREOF

FIELD

The present disclosure relates to a surgical instrument (a knotting device for laparoscopic) and parts (needle set) thereof, and more particularly, the disclosure relates to a surgical instrument and a carrier assembly adapted for facilitating the process of suturing and tying a surgical knot in a laparoscopic surgery.

BACKGROUND

The process and the art of tying a surgical knot in a laparoscopic surgery is disclosed in the patent literature, Taiwanese Patent No. 1551261, entitled "Novel Laparoscopic Extracorporeal Knotting Pusher Device". The preferred embodiment described in the '261 patent is directed to having a surgical knot that is partially tied and is attached to a carrier assembly of the described device connected to a control apparatus. The device is inserted into a patient's body via the abdominal cavity and is adapted for facilitating the suturing process for a surgeon in an operation wherein the applied surgical material can be tightened via the control apparatus. Once the surgical material is tightened at the treatment site, deployment of the partially tied surgical material from the described device is then cut to provide a fixed and secure surgical knot at the treatment site to help recovery.

However, the device of the '261 Patent has the following drawbacks:

1. The device disclosed by the '261 patent has the carrier assembly inserted into a sleeve of the control apparatus along a lateral direction for operation, and a recess is defined in the sleeve of the control apparatus for holding the carrier assembly. However, the carrier assembly is easily disengaged from the recess in the course of operation due to the configuration and malleability of the device. To retain the carrier assembly in the recess and to prevent from the disengagement, an outer layer of sleeve is slidably interconnected to the sleeve of the control apparatus, and such configuration of the apparatus is superfluous and less desirable.

2. The insertion direction of the carrier assembly is solely limited to a lateral direction as a bar of the control apparatus is configured at an end of the sleeve impeding axial loading or insertion of the carrier assembly. Consequently, the sleeve of the device has to be lengthened to accommodate the interconnected outer sleeve making the configuration of the apparatus cumbersome and inconvenient.

SUMMARY OF THE DISCLOSURE

To solve the said problems, the main objective of the present disclosure is to provide a surgical instrument and parts thereof simplifying the configuration and to reduce the full length of the device allowing it being more desirable and operatable for suturing procedure in an operation.

The present disclosure provides a carrier assembly comprising:

a body having two ends, a bar at a first end of the body and an engagement recess at a second end of the body located opposite to the bar; and a tubular member as an axial sleeve is securely interconnected inside the body.

Further, the present disclosure provides a surgical instrument including:

a grip having a central axle;

an L-shaped control recess defined in the grip having a horizontal and a vertical recess section;

a connection tube protruding from a side of the grip;

a transmission assembly interconnected with the grip and the connection tube, comprising a pulling rod slidably attached inside the connection tube, wherein the pulling rod has a conical engagement head at a first end and a coupling edge at a second end; a control member attached to the grip and is mobile around the central axle and shifts relatively along the L-shaped control recess of the grip and interconnected to the coupling edge; a connection portion interconnected around the central axle; a driving portion having a first portion interconnected with the connection portion and a second portion visibly shown on an outer surface of the grip; a torsion spring attached around the central axle, wherein the torsion spring having a first end abutting the grip and a second end abutting the control member; a resilient member interconnected in the connection tube and around the pulling rod, wherein the resilient member having a first end abutting the control member and a second end abutting the pulling rod at a position being adjacent to the conical engagement head; and a carrier assembly detachably connected to the control assembly, comprising:

a body having two ends, a bar at a first end of the body and an engagement recess at a second end of the body located opposite to the bar; and a tubular member as an axial sleeve securely interconnected inside the body.

In accordance, the reconfiguration of the bar at the first end of the body of the carrier assembly now permits the carrier assembly being flexibly attached and/or loaded to the connection tube. As such, the present disclosure provides a reduced length and streamlined surgical instrument and parts thereof resolving the problems associated with the outer layer of sleeve of the prior art. Accordingly, the present disclosure is not only labor-saving but also with improvements in the configuration for single-handed operation to facilitate its ease of usage for a surgical procedure under a constrained operation space such as laparoscopic surgeries.

DETAILED DESCRIPTION OF THE DISCLOSURE

Figure 1:
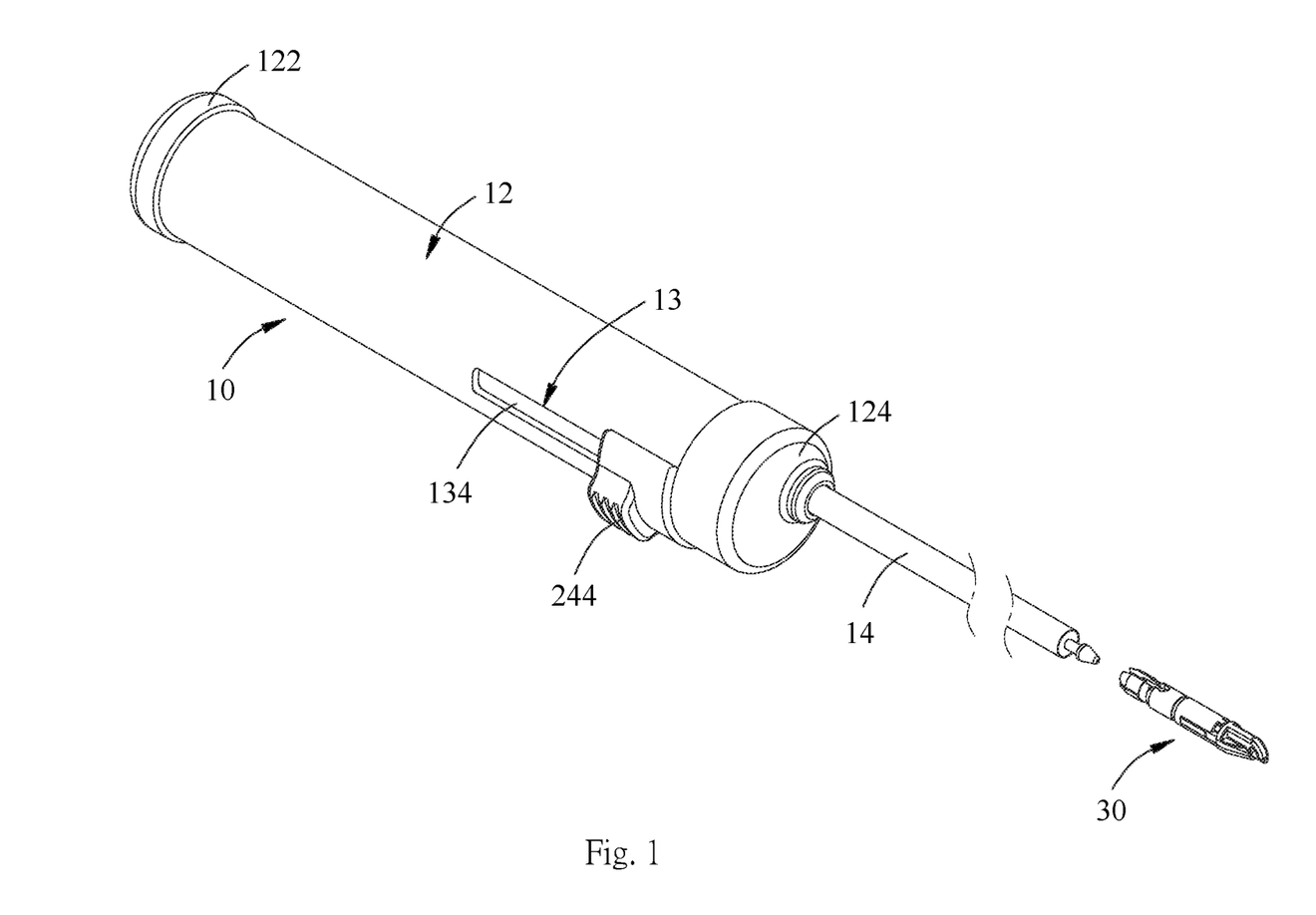
FIG. 1 is a perspective view of a surgical instrument in accordance with the present disclosure.
Figure 2:
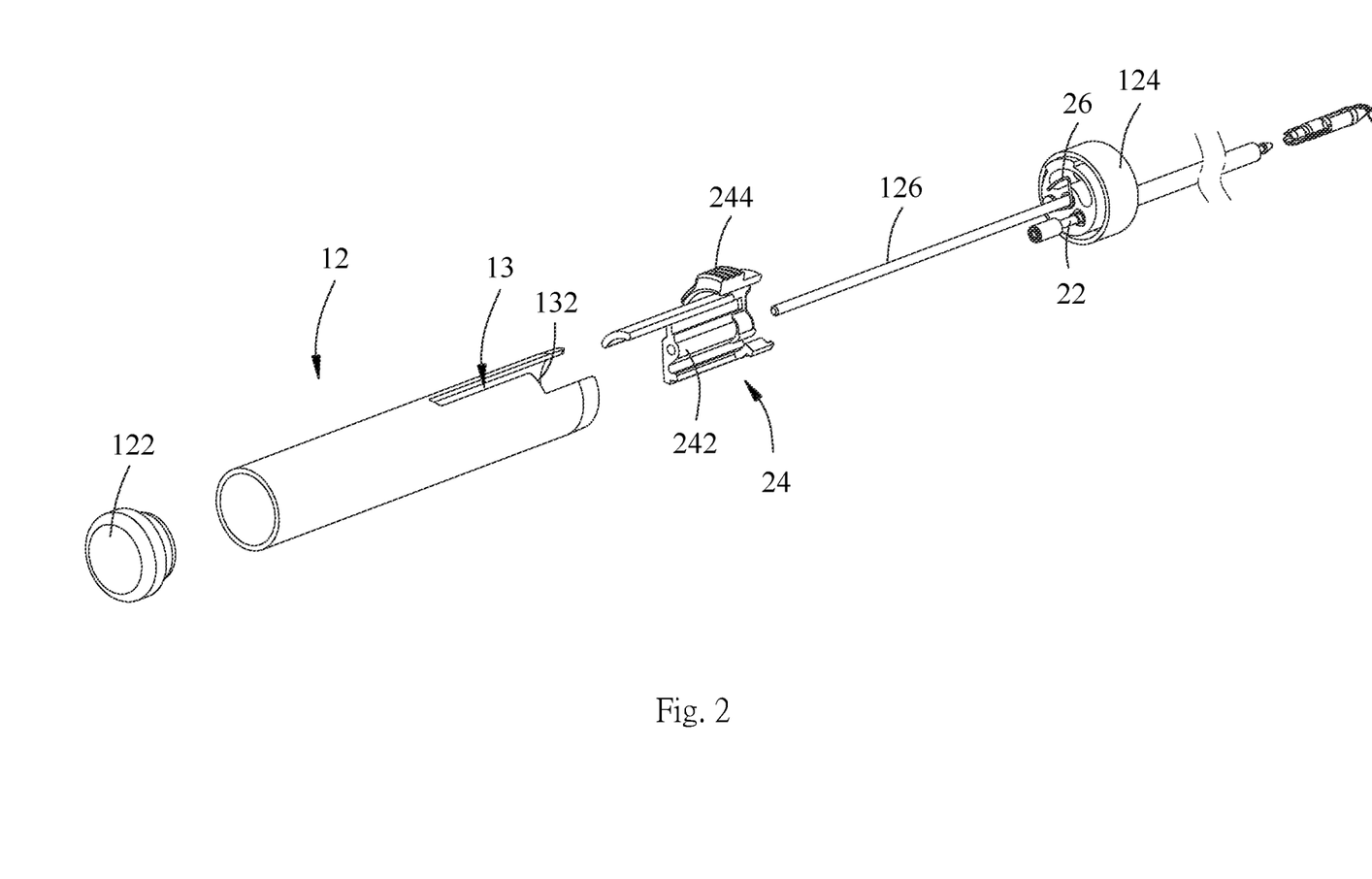
FIG. 2 is a partially exploded perspective view of the surgical instrument in accordance with the present disclosure.
Figure 3:
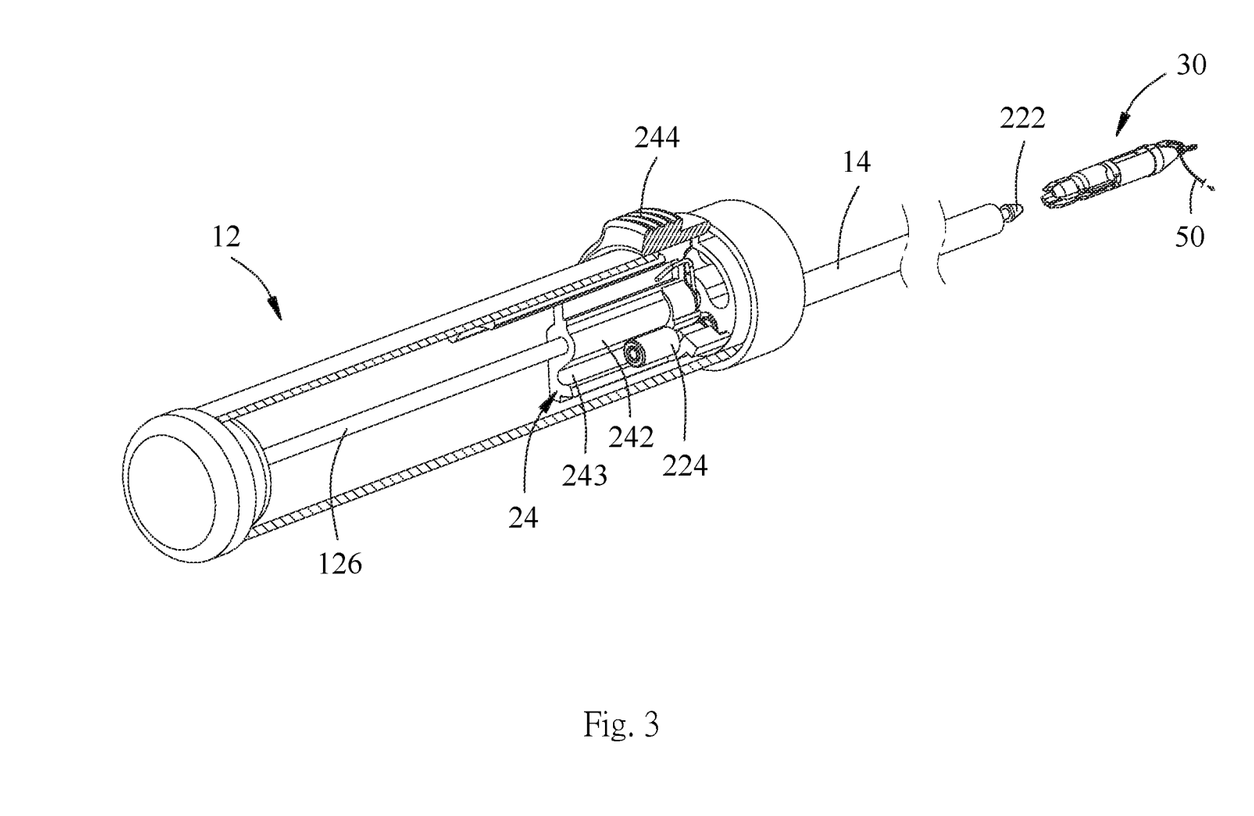
FIG. 3 is a sectional view of the surgical instrument in accordance with the present disclosure.

The present disclosure relates to a surgical instrument and parts thereof. With reference to FIGS. 1 to 3, the surgical instrument comprises a control assembly 10 and a carrier assembly 30. The carrier assembly 30 is interconnected with a partially tied surgical material 50, wherein the surgical material 50 is secured at the front end of the carrier assembly 30. In a preferred embodiment, the surgical material 50 is a partially tied surgical knot with a pre-tied loop readily for fastening. The surgical instrument is operable and/or controlled via the control assembly 10 to release or tighten the surgical material 50 at a treatment site.

The control assembly 10 comprises a grip 12, a connection tube 14, and a transmission assembly 20. The grip 12 is a hollow sleeve member with two open ends, wherein a cover 122 is attached to a first end, and a plug 124 is attached to a second end. The connection tube 14 is interconnected with the plug 124 and extends outwardly away from the control assembly 10, and a central axle 126 coaxially extending inwardly inside the grip 12 and interconnected to the plug 124.

The transmission mechanism 20 is interconnected in the grip 12, wherein the transmission mechanism 20 comprises a pulling rod 22, a control member 24, a torsion spring 26 and a resilient member 28. The pulling rod 22 is slidably affixed in the connection tube 14 having a conical engagement head 222 at a first end, and a coupling edge 224 at a second end. Preferably, the conical engagement head 222 is located at a far end of the pulling rod 22 away from the grip 12. And more preferably, the coupling edge 224 extends through the plug 124 and into the grip 12 and is at an opposite end of the conical engagement head 222 with a larger diameter than the pulling rod 22. The control member 24 is attached to the grip and is mobile around the central axle 125. The coupling edge 224 and the pulling rod 22 are engaged to the control member 24 allowing parallel movements of the pulling rod 22 with the control member 24. In some preferred embodiments, the control member 24 comprises a connection portion 242 interconnected around the central axle 126 and a driving portion 244 having a first section interconnected with the connection portion 242 and a second section visibly shown on an outer surface of the grip 12 for a user. Preferably, the connection portion 242 has a sliding groove 243 to accommodate the pulling rod 22 and movements thereof. Yet, in some preferred embodiment, an L-shaped control recess 13 is defined on the grip, comprising a horizontal recess section 132 and a vertical recess section 134. The control member 24 can be operated and/or shifted along the L-shaped control recess 13 of the grip 12. The torsion spring 26 is interconnected to the central axle 126, wherein the torsion spring 26 having a first end abutting the grip 12 and a second end abutting the control member 24 to provide a force pushing and shifting the control member 24 to the horizontal and/or recess section 132, 134 of the control recess 13 when required. The resilient member 28 is interconnected in the connection tube 14 and around the pulling rod 22, wherein the resilient member 28 having a first end abutting the control member 24 and a second end abutting the pulling rod 22 at a position being adjacent to the conical engagement head 222. In this regard, the resilient member 28 could be a compression spring for facilitating such function.

Figure 4:
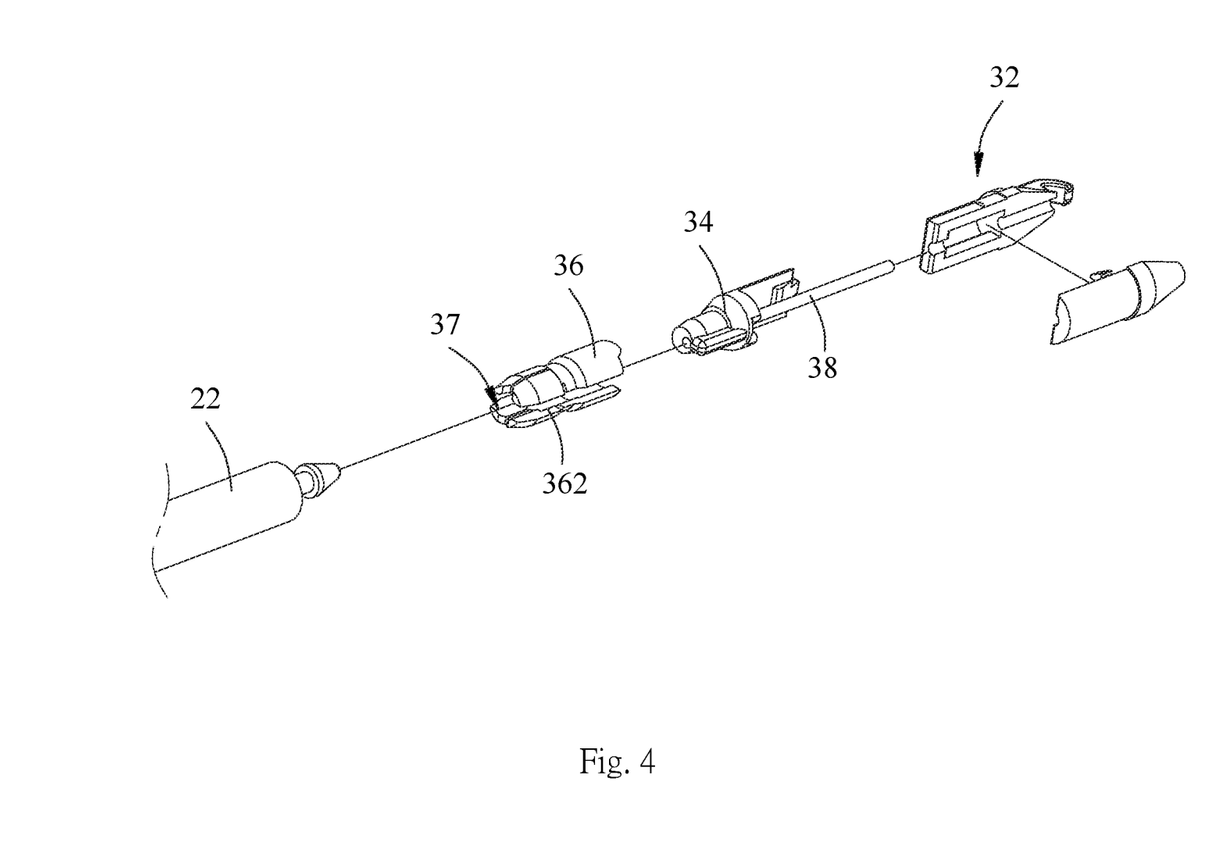
FIG. 4 is an exploded sectional view of the carrier assembly in accordance with the present disclosure.
Figure 5:
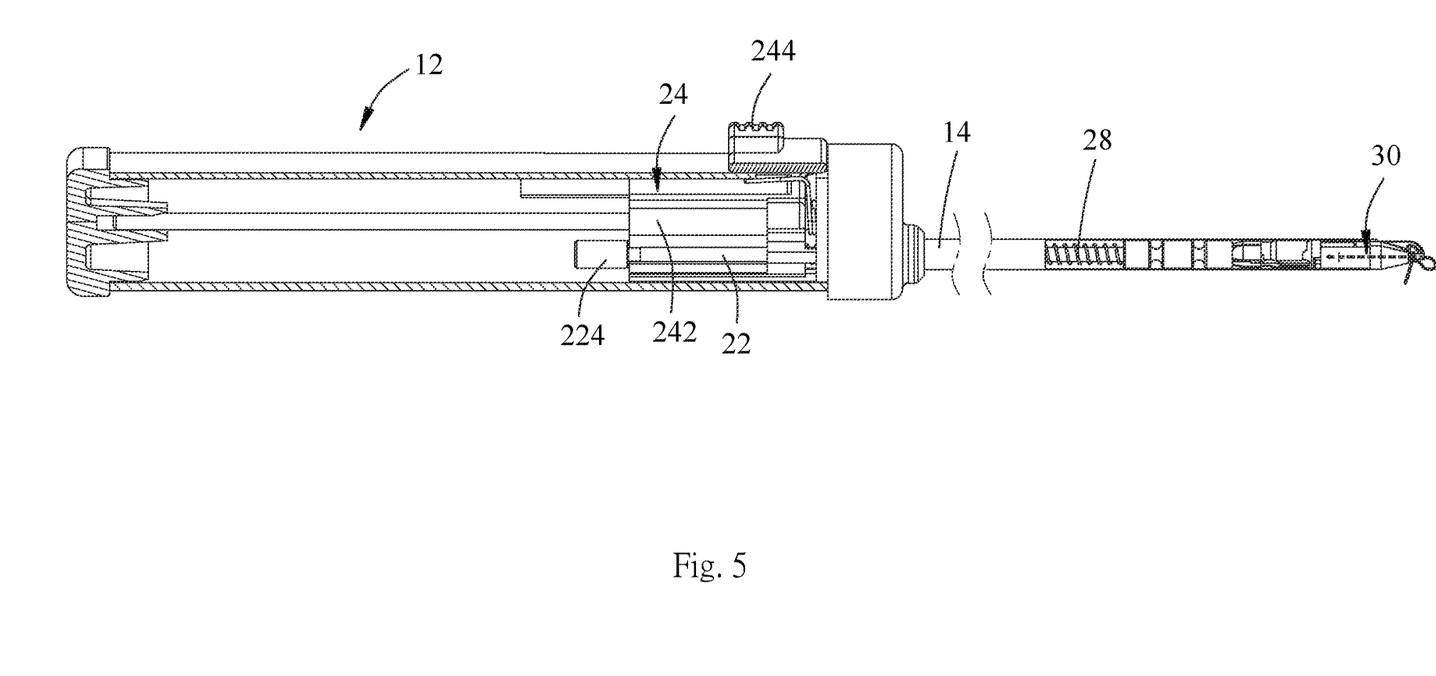
FIG. 5 is a sectional view from top of the surgical instrument in accordance with the present disclosure.
Figure 6:
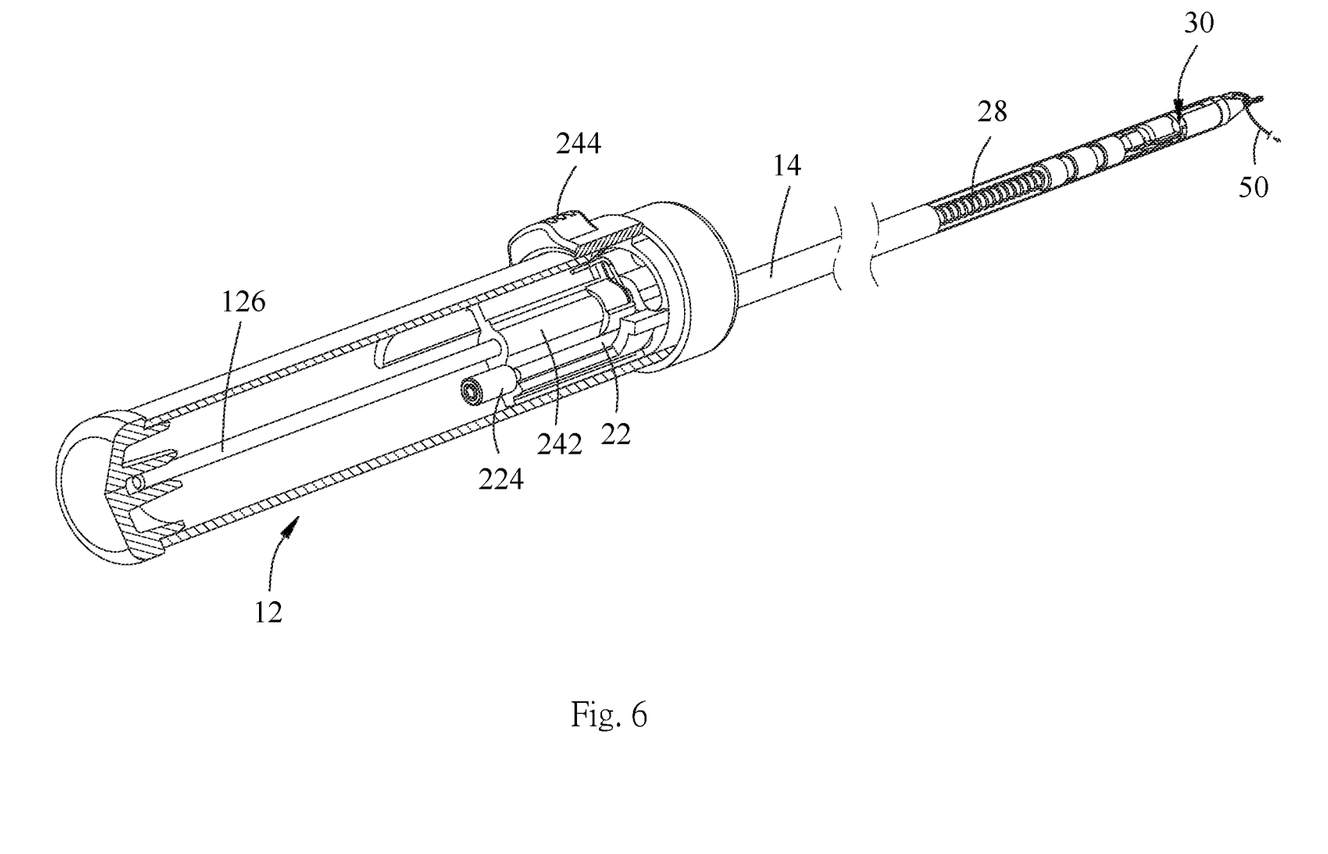
FIG. 6 is a sectional view of the surgical instrument in operation in accordance with the present disclosure showing engagement of the carrier assembly in the connection tube.
Figure 7:
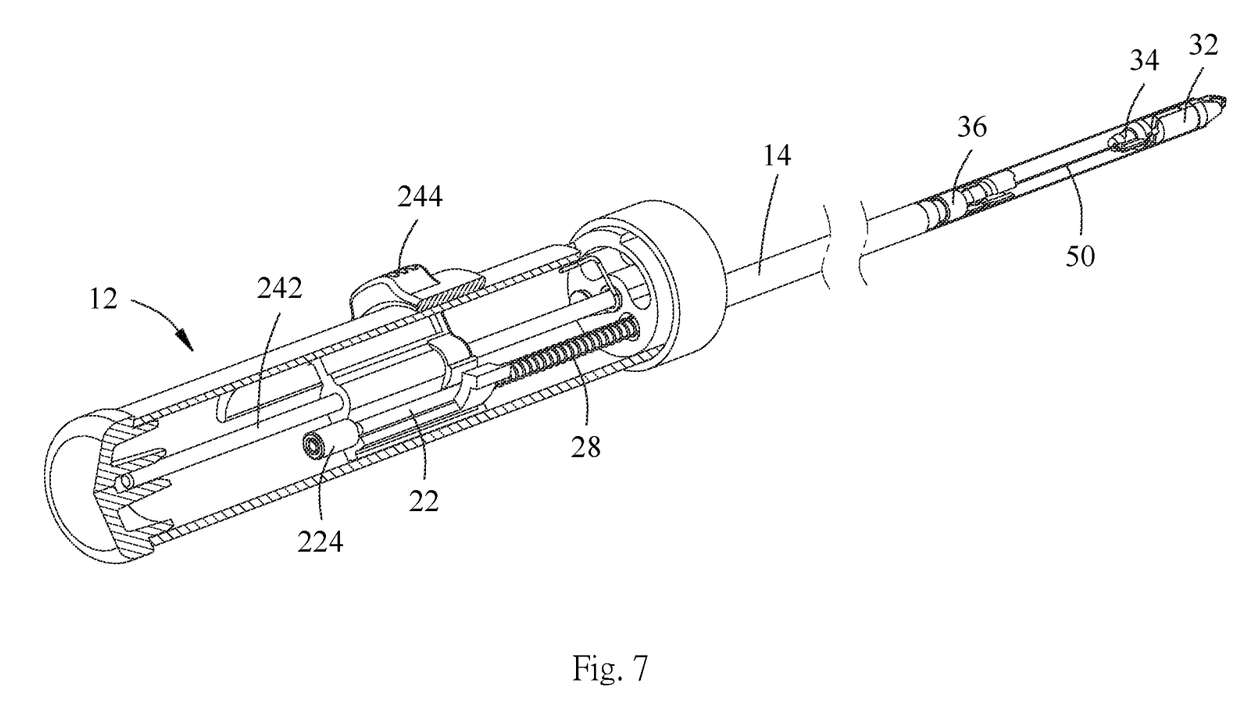
FIG. 7 is a sectional view of the surgical instrument in operation in accordance with the present disclosure showing the shifting of the driving portion along the L-shaped control recess.

With reference to FIG. 4, the carrier assembly 30 comprises a body having two ends and an axial sleeve 38 therein. The carrier assembly 30 has an engagement recess 37 that is selectively and/or adapted for receiving the conical engagement head 222 of the pulling rod 22. The axial sleeve 38 is securely interconnected inside the carrier assembly 30. Preferably, the axial sleeve 38 is a tubular member to accommodate a surgical material 50 extending therethrough. In some preferred embodiments, the axial sleeve 38 is adapted to accommodate a plurality of surgical sutures. In one of the preferred embodiments, the carrier assembly 30 comprises a head 32, a waist 34 and a tail 36. The bar 31 is located at an end of the head 32, the waist 34 connects the head 32 at its first end and the tail 36 at its second end. The tail 36 has a first end interconnected to the waist 34 and the engagement recess 37 is defined at the second end of the tail 36. In another preferred embodiments, the head 32 may be composed of two halves and/or more parts thereof. Alternatively, the head 32 and the waist 34 are integrally connected with each other as a single member. In one of the preferred embodiments, a plurality of resilient apertures 362 is defined longitudinally at the tail 36 with the engagement recess 37. Preferably, the head 32, the waist 34 and the tail 36 is detachable from one another to accommodate a particular configuration preferred by the user for operation.

With reference to FIGS. 1 and 3, the surgical instrument's initial position before operation is shown. The driving portion 244 is held at the horizontal recess section 132 of the control recess 13 by the force provided from the torsion spring 26, and the conical engagement head 222 protrudes from an end of the connection tube 14 by the force provided from the resilient member 28. The movements of the control member 24 are limited relatively to the grip 12 as its closely abutting and interconnected to the vertical and horizontal recess section 132, 134. Moreover, the control member 24 also support maintaining the pulling rod 22 in position.

With references to FIGS. 2 and 5 to 7, the axial sleeve 38 accommodates a surgical material 50 therein and the surgical material 50 is securely interconnected with the carrier assembly 30. The conical engagement head 222 is configured to be plugged to the engagement recess 37. Once the control assembly 10 and the carrier assembly 30 are engaged, the driving portion 244 then became active for maneuvering the movements of the pulling rod 22 and able to modulate and/or tightens the surgical sutures 50 along the connection tube 14. Whilst the coupling edge 224 maintains relatively engaged to the control member 24, the resilient member 28 contracts and/or expands, subject to the direction of the movement, providing forces for the pulling rod 22 to shift along the sliding groove therein. Therefore, the control assembly 10 also provides a means to assist the user to ensure that the surgical instrument is ready for operation, and for attuning and modulating of the surgical instrument in operation.

Once the user confirms the surgical instrument is ready for operation, it may then be inserted into the body of a patient via an incision in the abdominal wall and applying the surgical suture 50 for the purpose of stitching and repairing of the wound and/or treatment site. The complete closure of the surgical suture 50 delivers a secure and fixed surgical knot for the holding the treatment site in a simple fashion. The surgical suture 50 comprises a pre-tied loop for receiving the sutures 50 therein as the stitching is complete, the user regulates the closure by maneuvering the driving portion 244 along the vertical recess section 132 towards user, bringing about the pulling rod 22 moving in a direction towards the user as the loop tightens and closes. Once the surgical suture 50 fully tightens, it then becomes a secure surgical knot for holding the treatment site. The sutures 50 are then trimmed at a relatively close position to the surgical knot for fixing. The surgical instrument is then removed from the body and the user then has the option to move the driving portion 244 to the horizontal recess section 132 to disengage the carrier assembly 30 and attaching a new carrier assembly 30 for the next application. The disengagement is enabled from the rotation of the control member 24 relatively abutting the central axle 126 with forces provided by the torsion spring 26. The resilient member 28 provides forces to return the pulling rod 22 to an initial position wherein the conical engagement head 222 is exposed from the connection tube 14 and simultaneously detach the carrier assembly 30 from the pulling rod 22. Accordingly, the pulling rod 22 having a freed conical engagement head 222 is readily to be engaged to a new carrier assembly 30 for next treatment site.

With the reconfiguration of the surgical instrument, the bar 31 is now located at the first end of the body of the surgical instrument, and the carrier assembly 30 is configured having a mouth and/or an engagement recess 37 to attach to the pulling rod 22 and to further securely held in the connection tube 14 to avoid inadvertent disengagement. As such, the present disclosure provides removal of the superfluous outer layer of sleeve from the connection tube 14 allowing a simplified structure. Further, the surgical instrument is greatly reduced in length and thereby enhanced the operability of the instrument and easing the manufacturing process and costs in comparison to the previous art.

The surgical instrument can be operated single-handedly, wherein the closure or extension of the suture 50 may be conveniently maneuvered and controlled from a thumb of the user, and/or any other fingers that the user embrace. Further, the detachment between the carrier assembly 30, the pulling rod 22 and the connection tube 14 is made simple. It only requires the user to sleekly slide the driving portion 244 to the horizontal recess section 132 for detachment, wherein the meticulously calibrated forces provided by the torsion spring 26 and the resilient member 28 permits a comfortable and smooth movement of the driving portion 244 along the control recess 13 in the course of operation.

Even though numerous characteristics and advantages of the present disclosure have been set forth in the foregoing description, together with details of the structure and function of the embodiments. The specific embodiments discussed are merely illustrative of specific ways to make and use of the embodiments only. The present disclosure is not limited to the precise arrangements shown, and changes may be made in detail, especially in matters of shape, size, and arrangement of parts within the principles of the invention to the full extent indicated by the broad general meaning of the terms in which the appended claims are expressed.

REFERENCED NUMBER LIST 10 control assembly
12 grip
122 cover
124 plug
126 central axle
13 control recess
132 horizontal recess section
134 vertical recess section
14 connection tube
20 transmission assembly
22 pulling rod
222 conical engagement head
224 coupling edge
24 control member
242 connection portion
243 sliding groove
244 driving portion
26 torsion spring
28 resilient member
30 carrier assembly
32 head
32 bar
34 waist
36 tail
37 engagement recess
38 axial sleeve
50 surgical material

What is claimed is:

1. A carrier assembly for a surgical instrument, comprising:
   a body having two ends, a bar at a first end of the body and an engagement recess at a second end of the body located opposite to the bar; and
   a tubular member as an axial sleeve securely interconnected inside the body, wherein the body comprises a head, a waist and a tail detachably connected to each other, wherein the bar is located at a first end of the head and a second end of the head connects to the waist, the waist connects the head at a first end of the waist and a second end of the waist connects to the tail, the tail connects the waist at a first of the tail and a second end of the tail is the engagement recess, and the axial sleeve is interconnected within the waist, wherein the head is composed of two halves.

2. The carrier assembly according to claim 1, wherein the head and the waist are integrally connected with each other as a singular member.

3. The carrier assembly according to claim 1, wherein a plurality of resilient apertures is defined longitudinally at the tail with the engagement recess.

4. The surgical instrument for laparoscopic surgery, comprising:
   a grip having a central axle;
   an L-shaped control recess defined in the grip having a horizontal and a vertical recess section;
   a connection tube extending outwardly away from the grip;
   a transmission assembly interconnected with the grip and the connection tube, comprising:
      a pulling rod slidably attached inside the connection tube,
      wherein the pulling rod has a conical engagement head at a first end and a coupling edge at a second end;
   a control member attached to the grip and is mobile around the central axle and shifts relatively along the L-shaped control recess of the grip interconnected to the coupling edge;
   a connection portion interconnected around the central axle;
   a driving portion having a first portion interconnected with the connection portion and a second portion visibly shown on an outer surface of the grip;
   a torsion spring attached around the central axle, wherein the torsion spring have a first end abutting the grip and a second end abutting the control member;
   a resilient member interconnected in the connection tube and around the pulling rod, wherein the resilient member having a first end abutting the control member and a second end abutting the pulling rod at a position being adjacent to the conical engagement head; and
   a carrier assembly detachably connected to the control assembly, comprising:
      a body having two ends, a bar at a first end of the body and an engagement recess at a second end of the body located opposite to the bar; and a tubular member as an axial sleeve securely interconnected inside the body, wherein the body comprises a head, a waist and a tail detachably connected to each other, wherein the bar is located at a first end of the head and a second end of the head connects to the waist, the waist connects the head at a first end of the waist and a second end of the waist connects to the tail, the tail connects the waist at a first of the tail and a second end of the tail is the engagement recess, and the axial sleeve is interconnected within the waist, wherein the head is composed of two halves.

5. The surgical instrument according to claim 4, wherein the grip is a hollow sleeve member, a cover is attached to a first end and a plug is attached to a second end for sealing and the central axle coaxially extending inwardly inside the grip and interconnected to the plug.

6. The surgical instrument according to claim 4, wherein the connection portion having a sliding groove to accommodate the pulling rod and movements thereof.

7. The surgical instrument according to claim 4, wherein the head and the waist are integrally connected with each other as a singular member.

8. The surgical instrument according to claim 4, wherein a plurality of resilient apertures is defined longitudinally at the tail communicating with the engagement recess.

9. The surgical instrument according to claim 7, wherein a plurality of resilient apertures is defined longitudinally at the tail communicating with the engagement recess.

\* \* \* \* \*